(12) United States Patent
Kalkbrenner et al.

(10) Patent No.: US 9,588,328 B2
(45) Date of Patent: Mar. 7, 2017

(54) WIDE-FIELD MICROSCOPE AND METHOD FOR WIDE-FIELD MICROSCOPY

(75) Inventors: Thomas Kalkbrenner, Jena (DE); Ralf Wolleschensky, Jena (DE); Ingo Kleppe, Jena (DE)

(73) Assignee: Carl Zeiss Microscopy GMBH, Jena (DE)

( * ) Notice: Subject to any disclaimer, the term of this patent is extended or adjusted under 35 U.S.C. 154(b) by 522 days.

(21) Appl. No.: 14/112,519

(22) PCT Filed: Mar. 5, 2012

(86) PCT No.: PCT/EP2012/053726
§ 371 (c)(1),
(2), (4) Date: Jan. 6, 2014

(87) PCT Pub. No.: WO2012/143164
PCT Pub. Date: Oct. 26, 2012

(65) Prior Publication Data
US 2014/0111633 A1    Apr. 24, 2014

(30) Foreign Application Priority Data
Apr. 20, 2011    (DE) .................. 10 2011 007 751

(51) Int. Cl.
*G02B 21/36* (2006.01)
*G01N 21/64* (2006.01)
(Continued)

(52) U.S. Cl.
CPC ....... *G02B 21/365* (2013.01); *G01N 21/6408* (2013.01); *G01N 21/6458* (2013.01);
(Continued)

(58) Field of Classification Search
CPC ........... G01N 21/6408; G01N 21/6458; G02B 21/16; G02B 21/367; G02B 21/361; G02B 27/58; G02B 21/365; H04N 5/372
(Continued)

(56) References Cited

U.S. PATENT DOCUMENTS 3,547,512 A    12/1970    Baer
4,736,110 A    4/1988    Awamura
(Continued)

FOREIGN PATENT DOCUMENTS

DE    1 918 704    10/1969
DE    35 86 383 T2    3/1993
(Continued)

OTHER PUBLICATIONS

Hess, Samuel T., et al., "Dynamic clustered distribution of hemagglutinin resolved at 40 nm in living cell membranes discriminates between raft theories," *PNAS*, vol. 104, No. 44, pp. 17370-17375, Oct. 30, 2007.
(Continued)

*Primary Examiner* — Christopher S Kelley
*Assistant Examiner* — Zhihan Zhou
(74) *Attorney, Agent, or Firm* — Christensen Fonder Dardi PLLC (57) ABSTRACT

A method for high-resolution PAL microscopy, wherein a sample field is imaged on a detector surface of a detector, the sample field is imaged into an image field which is smaller than the detector surface, and the image field on the detector surface is shifted, so that the same sample field is imaged in different positions located adjacent to one another on the image field in order to determine information about changes in the sample field.

22 Claims, 3 Drawing Sheets

(51) Int. Cl.
*G02B 21/16* (2006.01)
*G02B 27/58* (2006.01)
*H04N 5/372* (2011.01)

(52) U.S. Cl.
CPC ............ *G02B 21/16* (2013.01); *G02B 21/361* (2013.01); *G02B 21/367* (2013.01); *G02B 27/58* (2013.01); *H04N 5/372* (2013.01)

(58) Field of Classification Search
USPC .......................................................... 348/79
See application file for complete search history.

(56) References Cited

U.S. PATENT DOCUMENTS

| | | | |
|---|---|---|---|
| 5,233,197 A * | 8/1993 | Bowman | G01N 21/6458 250/461.1 |
| 5,777,732 A | 7/1998 | Hanninen et al. | |
| 6,049,352 A | 4/2000 | Allio | |
| 6,262,423 B1 | 7/2001 | Hell et al. | |
| 7,235,047 B2 | 6/2007 | MacAulay et al. | |
| 7,271,382 B2 | 9/2007 | Engelmann et al. | |
| 7,327,901 B2 | 2/2008 | Karlsson et al. | |
| 7,582,855 B2 | 9/2009 | Pfeiffer | |
| 7,586,086 B2 | 9/2009 | Lauer | |
| 7,864,314 B2 | 1/2011 | Betzig et al. | |
| 8,289,620 B2 | 10/2012 | Bobanovic et al. | |
| 8,294,728 B2 | 10/2012 | Steinert | |
| 2002/0030811 A1 * | 3/2002 | Schindler | G01N 21/6452 356/318 |
| 2002/0186874 A1 | 12/2002 | Price et al. | |
| 2006/0011824 A1 * | 1/2006 | Engelmann | G02B 21/002 250/238 |
| 2006/0012870 A1 | 1/2006 | Engelmann et al. | |
| 2006/0171846 A1 | 8/2006 | Marr et al. | |
| 2007/0194214 A1 * | 8/2007 | Pfeiffer | A61C 9/0066 250/216 |
| 2009/0242798 A1 | 10/2009 | Bewersdorf et al. | |
| 2009/0242801 A1 * | 10/2009 | Engelhardt | G01N 21/6458 250/459.1 |
| 2011/0036996 A1 * | 2/2011 | Wolleschensky | G01N 21/6458 250/459.1 |
| 2011/0226965 A1 * | 9/2011 | Wolleschensky | G01N 21/6458 250/459.1 |
| 2011/0284767 A1 * | 11/2011 | Wolleschensky | G02B 21/367 250/459.1 |
| 2011/0304723 A1 | 12/2011 | Betzig | |
| 2013/0155218 A1 | 6/2013 | Kalkbrenner et al. | |

FOREIGN PATENT DOCUMENTS

| | | |
|---|---|---|
| DE | 694 16 671 T2 | 9/1999 |
| DE | 695 11 903 T2 | 4/2000 |
| DE | 103 21 885 A1 | 12/2004 |
| DE | 10 2004 034 979 A1 | 2/2006 |
| DE | 10 2005 027 077 A1 | 5/2006 |
| DE | 600 22 546 T2 | 6/2006 |
| DE | 10 2005 047 261 A1 | 4/2007 |
| DE | 603 12 717 T2 | 12/2007 |
| DE | 10 2004 014 048 B4 | 10/2008 |
| DE | 60 2004 012 274 T2 | 3/2009 |
| DE | 10 2008 059 328 A1 | 6/2010 |
| DE | 10 2009 060 490 A1 | 6/2011 |
| EP | 0 898 783 B1 | 3/2002 |
| EP | 1 377 865 B1 | 1/2009 |
| WO | WO 2006/127692 A2 | 11/2006 |
| WO | WO 2010060515 A1 * | 6/2010 ............ G02B 21/367 |
| WO | WO 2010060545 A1 * | 6/2010 ......... G01N 21/6458 |

OTHER PUBLICATIONS

Egner, Alexander, et al., "Fluorescence Nanoscopy in Whole Cells by Asynchronous Localization of Photoswitching Emitters," *Biophysical Journal*, vol. 93, pp. 3285-3290, Nov. 2007.

"Cropped Sensor Mode," www.andor.com/learning/digital_cameras/?docid=794, 2 pages.

Betzig, Eric, et al., "Imaging Intracellular Fluorescent Proteins at Nanometer Resolution," *Science*, vol. 313, 36 pages, Sep. 15, 2006.

Hess, Samuel T., et al., "Ultra-High Resolution Imaging by Fluorescence Photoactivation Localization Microscopy," *Biophysical Journal*, vol. 91, pp. 4258-4272, Dec. 2006.

Rust, Michael J., et al., "Sub-diffraction-limit imaging by stochastic optical reconstruction microscopy (STORM)," *Nature Methods*, Advance Online Publication, 3 pp., Aug. 9, 2006.

Shroff, Hari, et al., "Dual-color superresolution imaging of a genetically expressed probes within individual adhesion complexes," *PNAS*, vol. 104, No. 51, pp. 20308-20313, Dec. 18, 2007.

* cited by examiner

WIDE-FIELD MICROSCOPE AND METHOD FOR WIDE-FIELD MICROSCOPY

PRIORITY CLAIM

The present application is a National Phase entry of PCT Application No. PCT/EP2012/053726, filed Mar. 5, 2012, which claims priority from German Application Number 102011007751.0, filed Apr. 20, 2011, the disclosures of which are hereby incorporated by reference herein in their entirety.

FIELD OF THE INVENTION

The invention relates to a method for high-resolution PAL microscopy, wherein a sample field is imaged onto a detector surface of a detector. The invention likewise relates to a wide-field microscope for high-resolution PAL microscopy, having a detector which has a radiation-sensitive, spatially-resolving detector surface, an imaging lens system which images a sample field onto the detector surface of the detector, and a control device which reads out the detection data of the detector.

In wide-field microscopy, the physical laws of optical imaging basically determine resolution. As is known, the term diffraction limit is also used. For some time, different methods have been developed and used to overcome this diffraction limit in microscopy, in particular luminescence or fluorescence microscopy (here, luminescence is understood, as is generally usual, as a generic term for phosphorescence and fluorescence).

A method which achieves a resolution beyond the diffraction limit is known, for example, from WO 2006/127692. A method according to the preamble and a microscope according to the preamble are described there. The method abbreviated to PALM (photo activated light microscopy) uses a label which can be activated by means of optical radiation. Only in the activated state can the label then be excited to emit particular fluorescence radiation. Depending on the substance of the label, radiations of different wavelengths or radiation of one and the same wavelength can be used for the activation and the fluorescence excitation. Non-activated molecules of the label emit no, or at least no noticeable, fluorescence radiation even after irradiation by excitation radiation. The activation therefore brings about a switching and is, therefore, also called switching signal. In the PALM method, the switching signal is applied such that at least a certain proportion of the activated labels are spaced apart from neighbouring activated labels such that they are separated, as measured by the optical resolution of the wide field microscope used, or can be separated subsequently. The activated labels appear largely isolated in the recorded wide-field image. For these isolated labels, the center of their resolution-limited radiation distribution can be determined computationally and the position of the labels can be determined with higher precision than the wide-field microscope used actually allows. This increased resolution by computational determination of the center of the diffraction distribution is also called "super-resolution" in the technical literature.

For the isolation of individual labels, the methods used, of which the above-mentioned PAL microscopy is only one example, as a rule make use of the fact that the probability that a label is activated by the switching signal is the same for all labels. It is thereby possible to ensure that the probability of activating labels present in a given unit area of the sample is so small that there are sufficiently large areas in which only spacially resolvable labels emit fluorescence radiation within the optical resolution of the wide-field microscope used. The result of a suitable configuration of the switching, for example, by suitable choice of the intensity of the switching signal, is that, as far as possible, only labels which are isolated in terms on the optical resolution of the wide-field microscope are activated and subsequently emit fluorescence radiation. The position determination therefore is the basis of a highly sensitive wide-field microscopy and achieves a highly precise localization of individual molecules in the nanometer range.

As only a subset of the labels of the sample is in the fluorescent state in a single image frame, the method is repeated very often, with the result that different stochastic subsets of the labels fluoresce in different single image frames. The different variants of this microscopy, which are also referred to by the abbreviations PALM, STORM, D-STORM, etc., mainly differ in the choice of the labels (molecules, fluorophores) and in the manner of the switching.

In order to reproduce a sample to be studied as completely as possible, the principle requires that a subset of the labels of the sample be brought into the fluorescent state, and that many frames (typically 5,000 to 20,000) of the sample be recorded in order to obtain as many different subsets of the fluorophores as possible and thus as many different frames as possible. This basic requirement of high-resolution wide-field microscopy disadvantageously leads to relatively long recording times for a complete image of the sample.

SUMMARY OF THE INVENTION

The object of the invention is therefore to specify a method for wide-field microscopy and a wide-field microscope with which a rapid image acquisition can be achieved for microscopy techniques in which a large number of frames of a sample field have to be recorded.

This object is achieved according to the invention with a method for high-resolution PAL microscopy, wherein a sample field is imaged onto a detector surface of a detector, wherein the sample field is imaged into an image field which is smaller than the detector surface, and the image field is shifted over the detector surface, with the result that the same sample field is imaged in different, adjacent positions of the image field in order to determine information about temporal changes in the sample field.

The object is likewise achieved by a wide-field microscope designed for high-resolution PAL microscopy, having a detector which has a radiation-sensitive, spatially-resolving detector surface, an imaging lens system which images a sample field onto the detector surface of the detector, and a control device which reads out detection data of the detector, wherein the imaging lens system images the sample field into an image field which is smaller than the detector surface, and comprises a controllable scanning device for shifting a position of the image field on the detector surface, wherein the control device controls the scanning device such that the same sample field is imaged in different, adjacent positions, and determines an item of information about temporal changes in the sample field on the basis of the detection data read out.

The invention starts from the knowledge that the time it takes to read out the data from the detector is a fundamental time-critical factor in the recording of series of frames. Although at a first glance it could be assumed that, e.g., in PALM the localization of the isolated molecules in a frame is also limiting in terms of time, the inventors found a close analysis that the duration of this method step can be reduced by increased outlay on computation. The exposure time on the camera that is likewise time-critical at first glance also proves to be substantially less critical when considered in detail, as the number of available photons per time unit can be improved by increasing the excitation intensity and choice of suitable molecules, which has a positive effect on the exposure time. However, the read-out process of the detector, which is also called a camera in the literature, itself requires an amount of time that is always present and which cannot be avoided.

The concept of the invention thus provides that one and the same sample field is imaged onto an image field, the position of which on the detector surface is adjusted. Unlike in the known laser-scanning microscopy, a detector is used which uses a two-dimensional spatial resolution that determines the optical resolution of the microscope. Naturally, a further substantial difference compared with laser-scanning microscopy is also that one and the same sample field is imaged repeatedly. In laser-scanning microscopy, on the other hand, different sample sections are imaged by scanning. In addition, laser-scanning microscopy images the imaged sample field in spatially-resolving manner, whereas the present invention is dedicated to wide-field microscopy.

Therefore, the imaging-beam path is scanned over the detector surface, with the result that the same sample field is imaged onto the detector surface several times in succession, namely on different, non-overlapping parts of the image field. In an embodiment of the invention, this allows the image field to be imaged onto the detector surface several times before the detector is read out. Each read-out process then covers several images, whereby the duration of the read-out time per image falls to the corresponding fraction.

In an embodiment, the read-out time per frame is reduced to a fraction of the read-out time of the detector used. This is achieved in that the shift of the position is synchronized to the read-out of the detector such that one read-out process reads out detection data comprising several different positions of the image field.

The position of the image field is particularly preferably shifted on the detection surface stepwise. Only after several shifts are the detection data read out. For the detection data read out, each position of the image field, i.e., each portion of the detector surface, is then allocated to a frame of the sample field.

If n different positions are used, n frames are obtained by one read-out process. The read-out time per frame then falls to the corresponding reciprocal 1/n.

In an alternative, a sensor is used, the detector surface of which is partially shaded. While for obtaining frames the image field is shifted from one portion to the next and then a frame is in turn recorded at the next portion in a non-shaded part, the charges of the previously-recorded image can be shifted into the shaded area in this concept. From there, they can then be transferred to the horizontal shift register for read-out. This allows an almost continuous read-out of the detector.

For this design, it is preferred to use as a detector a CCD surface detector which comprises a horizontal shift register on a read-out edge of its detector surface and the detector surface of which has a radiation-sensitive part and a part shaded from incidence of radiation which lies between the read-out edge and the radiation-sensitive part. To record frames, the image field is shifted in steps over the radiation-sensitive part of the detector surface. The detector is further controlled such that during the recording of subsequent frames obtained with a shifted image field charges of a frame produced are transferred to the part shaded from incidence of radiation and then from there into the horizontal shift register.

In a third concept, a detector is used which comprises at least two independently readable detector surface parts. The image field is placed on these in sequential manner. In the case of two detector surface parts, these are exposed alternately. One detector surface part can thereby be read out while another is being exposed. This likewise allows an almost continuous exposure, as the read-out times for a detector surface part arise while an image is already being recorded on another detector surface part.

For this embodiment, a method in which a detector is used which comprises several, adjacent, spatially resolving detector surface parts for each of which detection data can be read out independently. The image field is placed intermittently on alternating ones of the several detector surface parts. For each detector surface part, the detector surface data are read out, while the image field is placed on another of the several detector surface parts. Such detectors are in part produced using CMOS technology and are also called Active Pixel Sensors.

In order to record the frames in the different image field positions separately in the named embodiments, it is to be preferred to ensure that, as far as possible, no radiation is detected by the detector during the time in which the image field is moved into the next image field position. This can take place, for example, by inactivating an illumination beam path or an illumination beam source. The illumination is synchronized such that the sample is not illuminated or the sample is not excited or activated to emit fluorescence radiation during the shifting movement of the image field position. As an alternative or in addition, it is possible to provide a proper shadowing element in the imaging beam path which shadows the beam path during the shifting movement of the image field from one image field position into the next. Movable diaphragms, chopper wheels, AOTFs or suitable elements that switch off or deflect the beam path, such as LCD or DMD elements, etc. are possible shadowing elements or can be utilized for the shadowing. As a third option, a camera can be used, the detector of which can be switched to inactive during the shifting movement of the image field, with the result that the detector detects no radiation during the shifting movement. Naturally, the corresponding elements are suitably controlled by the control device in the wide-field microscope, wherein a combination of the named measures is, of course, also possible.

Finally, in a further option, it is possible to shift the image field in a continuous movement over the detector surface. Then, the images of the detected molecules are blurred by the scanning movement. However, with knowledge of the scanning movement, the intensity distribution can be reconstructed again for the necessary image evaluation.

In this configuration, for high-resolution PAL microscopy the image field is continuously shifted over the detector surface. The information about changes in the sample field is determined on the basis of taking the shift into consideration.

The shift of the image field over the detector surface is preferably marked in the image by adjusting a focus of the imaging according to a modulation which is synchronous with the shift. The focus adjustment changes the intensity distribution in the image data and allows the current shift to be determined directly from the image data.

The frames preferably correspond in each case to a subset of the fluorescent label molecules in the sample if the wide field microscopy method or the corresponding microscope is used in PAL microscopy or a version thereof. This can be achieved particularly easily in that the excitation or activation is effected synchronized to the shift of the position of the image field.

Where method features are described in this description, these features can be or are realized in the corresponding wide-field microscope by a suitable action of the control device. Therefore the disclosure of a method feature is likewise also regarded as a disclosure of a corresponding subject device feature within the meaning of a corresponding functional definition or property of the control device. Naturally, the disclosure of a functional feature of the control device is conversely likewise also to be seen as a disclosure of a corresponding method feature.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features of the invention in which.

DETAILED DESCRIPTION

Figure 1:
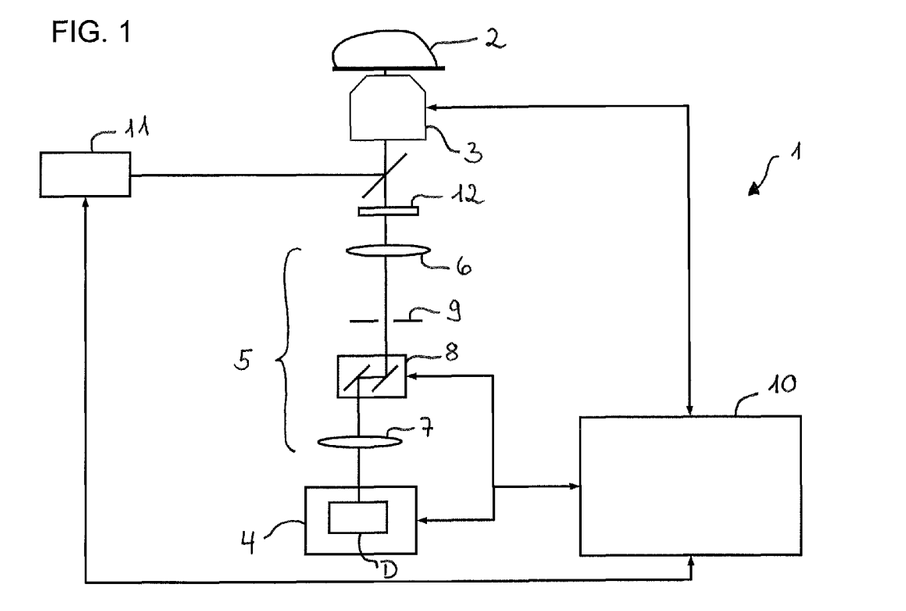
FIG. 1 depicts a schematic representation of a wide-field microscope which is designed to be suitable in particular for PAL microscopy, according to an embodiment.

FIG. 1 schematically shows a microscope 1 which images a sample 2 in wide-field imaging. The microscope 1 is particularly designed to detect a temporal change in the sample 2, such as is necessary, for example, within the framework of PAL microscopy. Where the wide-field microscope of FIG. 1, or modifications thereof, is described below with reference to PAL microscopy, this is to be understood merely by way of example or as relating to preferred but not exclusive embodiments. The wide-field microscope of FIG. 1, or developments and modifications thereof, can also be used advantageously in another connection when it is necessary to determine the temporal change of a sample at time intervals that are as small as possible, or even continuously.

The wide-field microscope 1 has an objective 3 which images the sample 2 onto a camera 4 which contains a detector D. This imaging is a known wide-field imaging, i.e., a sample field detected by the objective 3 on the sample 2 is imaged into an image field which lies on the detector D of the camera 4.

The wide-field microscope 1 comprises a scanning device 5 which shifts the position of the image field on the detector D. In the design shown, the scanning device 5 comprises a scanning lens system 6, 7 between which a scanner 8 is located which brings about a biaxial deflection. The scanner 8 is preferably located in or close to a pupil plane. Upstream of the scanner 8 in the imaging direction, there is a diaphragm 9 which lies in an intermediate image plane provided by the scanning lens system 6, 7 and thus defines the size and position of the image field on the detector D of the camera 4. To set the size and position, the diaphragm 9 can be designed to be adjustable in its size and/or to be movable.

The operation of the scanning device 5 and also of the camera 4 is controlled by a control device 10 which is connected to it and optionally to any further components via corresponding control lines. The control lines are illustrated in FIG. 1 by lines with double arrows. In the schematic representation of FIG. 1, the control engagement of the control device 10 with respect to the scanning device 5 is drawn in at the scanner 8. Naturally, this can alternatively or additionally also take place at the diaphragm 9 or a drive (not represented in the figure) for shifting and/or adjusting the size of the diaphragm 9.

For implementation of PAL microscopy, the microscope 1 additionally also has a radiation source 11 which irradiates the sample 2 via a beam splitter, not described in more detail, and the objective 3. In order to block reflections of the illumination radiation to the camera 4, an emission filter 12 in the imaging beam path is placed between the beam splitter and the camera 4.

In the microscope 1 the scanning device 5 effects that the image field on the camera 4 is much smaller than the radiation-detecting surface of the detector D in the camera 4. This is brought about by the diaphragm 9. Alternatively, it is also possible to form the imaging beam path in principle such that the sample field detected by the objective 3 is imaged onto an image field that is smaller than the detector surface.

Optionally, the diaphragm 9 is variable in order to adapt the image field imaged onto the sensor optimally to requirements (compromise between image field size and speed), or to the different variants explained below.

Figure 2:
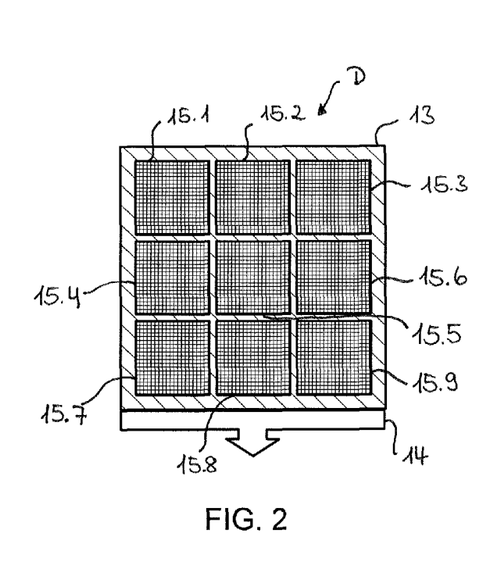
FIG. 2 depicts a top view of a detector surface of the microscope of FIG. 1 to illustrate the wide field image acquisition.

FIG. 2 shows one embodiment of the microscope 1 with regard to the detector D of the camera 4. The figure shows a top view of the detector surface 13. The detector D comprising the detector surface 13 is, for example, a CCD sensor which is read out via a horizontal shift register 14.

Figure 4:
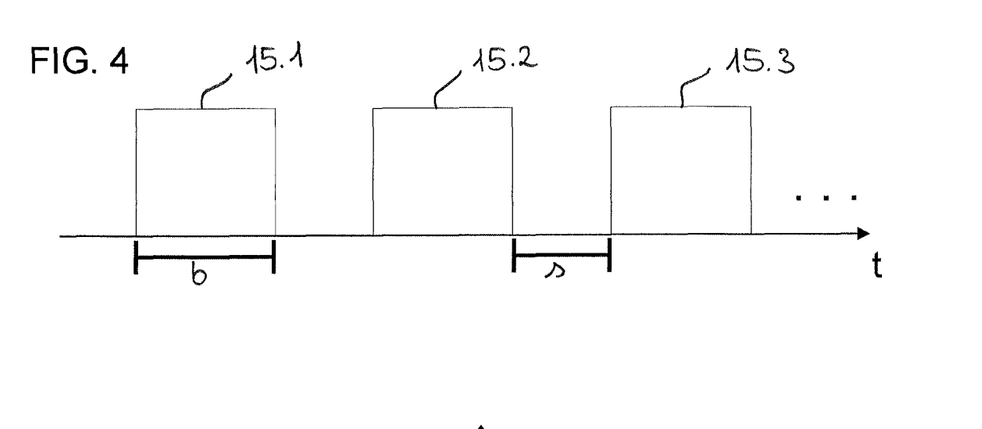
FIG. 4 depicts a time series to illustrate the image acquisition of the microscope of FIG. 1 with a detector with the design of FIG. 2.

As the read-out process, which converts the charges from the CCD sensor via the shift register 14 to detector signals which are delivered by the camera 4 to the control device 10, is a critical duration for the recording of a temporal change in the sample 2, the control device 10 on the microscope 1 controls an operation such that the position of the image field 15 is shifted over the detector surface 13. FIG. 2 shows nine different image field positions 15.1-15.9 of the image field 15. These positions comprise nine images of one and the same sample field of the sample 2 which are spaced apart in time and are exposed in sequence on the detector surface 13. FIG. 4 schematically shows the timing. The detector surface 13 is exposed in each of the image field positions 15.1, 15.2, 15.3, . . . over an exposure time b. Between the exposures, the image field 15 is shifted into the respectively new image field position, which requires a scanning time s. If the detector surface 13 was covered by the different image field positions 15.1-15.9, the detector signal is read out via the shift register 14 to detect the corresponding charges.

Each image field position 15.1-15.9 thus corresponds to a frame of one and the same sample field of the sample 2. The recording of nine frames thus needs a duration of 9*b plus 9*s plus the duration of the read-out process. The recording of an individual frame in the case of nine frames per read-out process thus requires a duration of b plus s plus a ninth of the read-out time. As the scanning time s is very much less than the read-out time, which is the dominant time element in usual cameras 4, a considerable acceleration of the frame acquisition is achieved by this procedure.

Naturally, the use of 9 image field positions is to be understood, not as absolutely necessary for this principle, but purely by way of example. Nor is it absolutely necessary for the frame positions, as represented in FIG. 2, to be spaced apart by a small gap. Rather, it is to be preferred to place the frame positions as close together as possible, wherein overlapping frame positions can sometimes also be admissible.

In the evaluation of the detector signals, the control device 10 deconstructs the complete image delivered by the camera 4 into the frames taking into account the previously-effected shift of the frame positions, in the present example the nine frames which correspond to the frame positions 15.1-15.9.

In order to record the frames in the different image field positions 15.1-15.9 as separately as possible, it is to be preferred to ensure that, as far as possible, no radiation is detected on the detector surface 13 during the scanning time s, thus during the time in which the image field 15 is moved into the next image field position. In PAL microscopy, or related or similar high-resolution microscopy methods, this can be done by synchronizing the shift to the illumination from the radiation source 11. The illumination is synchronized such that during the shift of the image field position no fluorescence radiation is excited, or the sample 2 is not activated to emit fluorescence radiation. As an alternative or in addition, it is possible to provide a corresponding shadowing element in the imaging beam path which shadows the beam path during the shift of the image field from one image field position into the next. For this, movable diaphragms, chopper wheels or elements that suitably switch off or deflect the beam path, such as LCD or DMD elements, etc., are options. It is also possible to use a camera 4, the detector D of which can be switched to be inactive during the shift of the image field from one image field position allocated to one frame into the image field position allocated to the next frame, with the result that the detector does not detect radiation during such intervals.

However, embodiments are also possible in which the shift of the image field 15 from one image field position into the next happens so quickly that radiation recorded during that intervals does not unduly distort the frames. There is then no need to make arrangements to shade or switch off the camera 4 or its detector D during this scanning step.

The scanning device 5 (or the scanner 8 in the described embodiment example) effects a stepwise shift of the image field 15 from one of the image field positions 15.1-15.9 into the next in each case. Due to this intermittent procedure, the image field positions 15.1-15.9 combine to fill the detector surface 13 as completely as possible.

Figure 3:
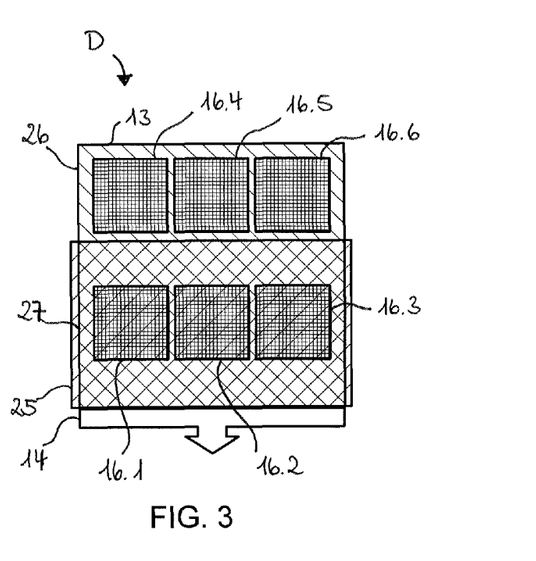
FIG. 3 depicts a representation similar to FIG. 2 for a microscope with modified detector, according to an embodiment.

FIG. 3 shows a modification of the microscope 1 in which detector D of the camera 4 allows an almost continuous signal read-out. For this, a part of the detector surface 13 is covered by a diaphragm 25. The diaphragm 25 lies on the edge with the shift register 14. The detector surface 13 thereby comprises an active part 26 which detects incident radiation, and a covered part 27 which lies between the shift register 14 and the active part 26. Charges can now be shifted continuously towards the shift register 14 through this covered part 27.

The control device 10 now controls the camera 4 or its detector D and the scanning device 5 such that the image field is shifted in steps over the active part 26. In the present example, three image field positions 16.4-16.6 are provided. As soon as the scanning process is complete, charges obtained in the image field positions, which in turn correspond to frames, are shifted into the covered part 27 of the sensor. This happens very much more quickly than the read-out on the horizontal shift register 14. In turn, frames can now be detected in three image field positions on the active part 26. In the meantime, the previously detected charges of the frames are shifted towards the horizontal shift register 14 and read out there. FIG. 3 shows the state after three frames corresponding to image field positions 16.1-16.3 have been first recorded in the active part 26 and then shifted into the shaded part 27. While these are then transferred to the horizontal shift register 14 and read out there, three further image field positions 16.4-16.6 or associated frames are recorded next.

The development according to FIG. 3 allows an almost continuous recording of frames. A further advantage of this variant is that the scanner 8 need only be designed as a uniaxial scanner, as the position of the image field only has to be shifted along one axis, namely parallel to the shift register 14.

In other respects, the features described with reference to FIG. 2 also apply to the detector or camera modification according to FIG. 3.

Figure 5:
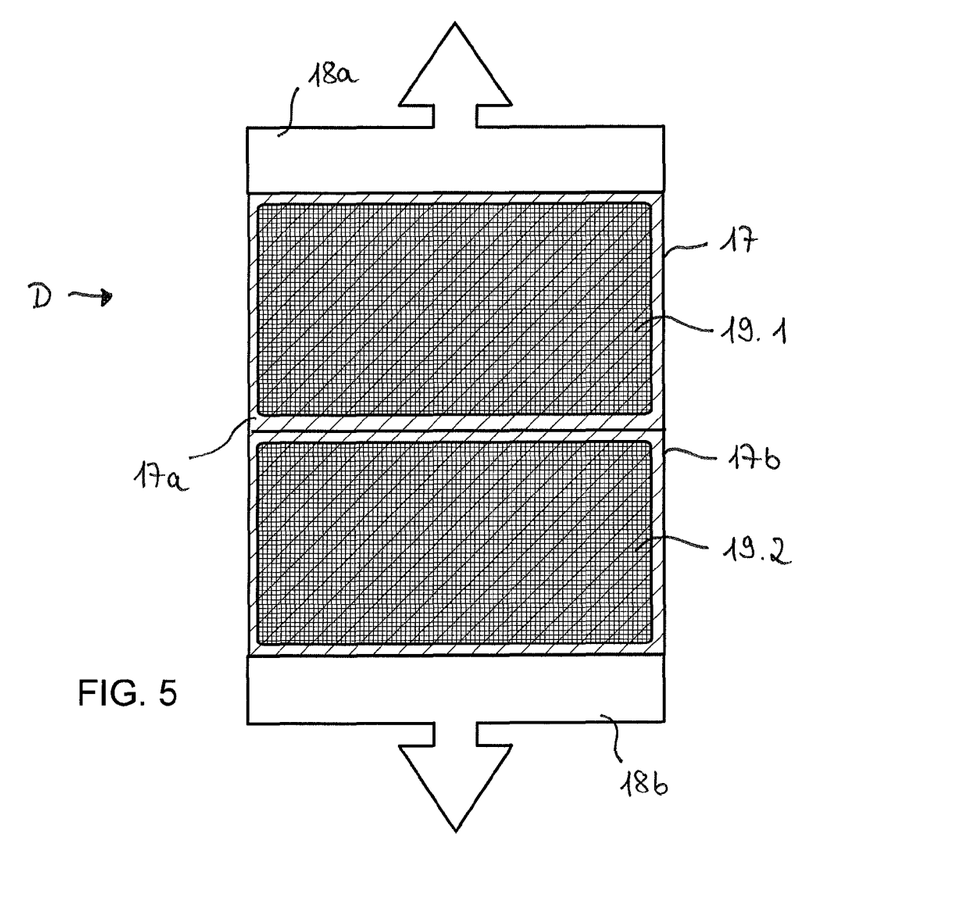
FIG. 5 depicts a representation similar to FIGS. 2 and 3 for a further variant of the detector of the microscope of FIG. 1.

FIG. 5 shows a further variant with regard to the camera 4 or its detector D. This now has a detector surface 17 which comprises two parts 17a and 17b. The detector part surfaces 17a and 17b each have a read-out device of their own, e.g., a shift register 18a and 18b of their own, and can thus be read out independently of each other. The control device 10 now controls the shift of the image field between two image field positions 19.1 and 19.2, with the result that the detector part surfaces 17a and 17b are exposed alternately. While the detector part surface 17a is exposed, the detector signal is read out at the detector part surface 17b via the read-out device, which is realized here by the shift register 18b. This applies analogously while the detector part surface 17b is exposed. This alternating exposure of the detector part surfaces 17a and 17b likewise allows an almost continuous data acquisition. If the read-out time via the read-out devices of the detector part surfaces 17a and 17b lasts longer than the image acquisition for a frame, the development of FIG. 5 can be combined with that of FIG. 2 by exposing each detector part surface 17a and 17b separately in the manner used for the detector surface 13 of FIG. 2. More than two detector part surfaces can also be used. Such sensors are produced, e.g., as CMOS sensors and can be so-called Active Pixel Sensors.

As described above, it is possible to produce the frames with synchronized exposure (by switching off the illumination or blocking the illumination beam path, by blocking the imaging beam path or by deactivating the detector), such that no radiation is recorded during the shift of the image field into the new image field position. However, as described below with reference to FIGS. 6 to 9, an intentionally continuous shift of the image field accompanied by continuous exposure can also be utilized. This is shown schematically by FIG. 6.

Figure 6:
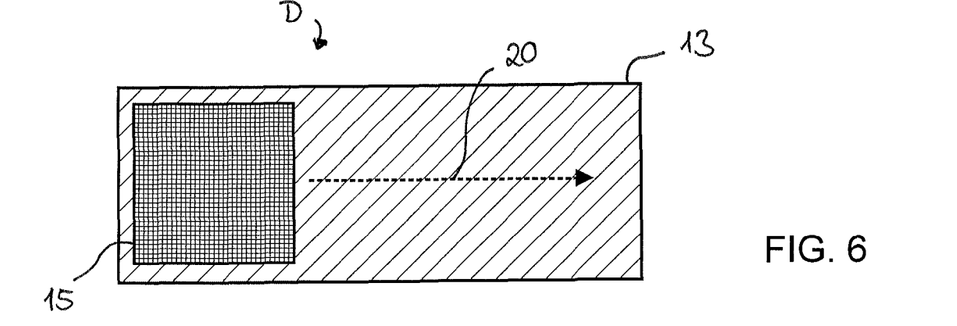
FIGS. 6-8 depict views of a detector or a detector field similar to that of FIG. 2 for a further modification of the microscope of FIG. 1.

The image field 15 is continuously shifted over the detector surface 13 along a shift direction 20. During the shift, the detector surface 13 picks up radiation. The thus-obtained image is shown schematically by FIG. 7, which represents a reference framework 22 which corresponds to the detector surface 13 in the recorded detector data.

Figure 7:
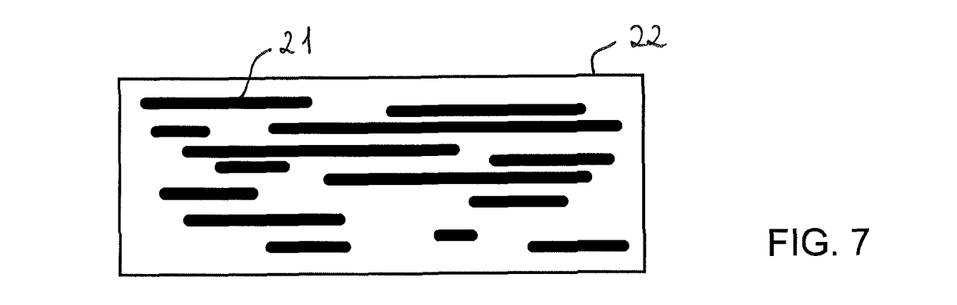
Figure 8:
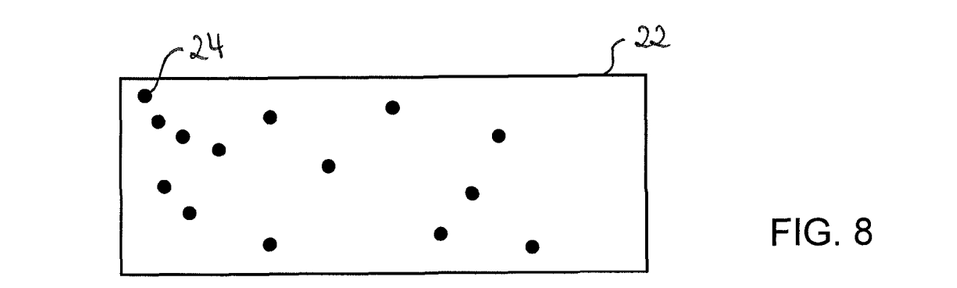

In the reference framework 22, individual luminous dots of the sample field are stretched to form light trails 21 along the shift direction 20. The start of such a light trail 21 is the time at which an image point begins to emit fluorescence radiation. The end of a light trail marks the time at which the emission of fluorescence radiation ends on the dot in question. As the individual luminous image points (which are also called "beacons" in PAL microscopy) are sufficiently separated in the high-resolution measurement methods of interest here, with the result that the light trails 21 as a rule do not overlap, it is easily possible to generate from the light trails 21 individual illuminated dots 24 which correspond to those points in the reference framework 22 at which the illuminated dot lit up. This state of the image processing is shown by FIG. 8.

In a next step, these illuminated dots 24 must now be corrected with regard to the continuous shift of the image field 15. For example, the control device takes into account the fact that the reference framework 22 corresponds to a time axis in a horizontal direction, which is determined by the shift of the image field 15. Thus, because of the known shift of the image field 15, for each horizontal coordinate, the relative coordinate in the image field 15 can be indicated, i.e., the point in the image field at which the illuminated dot 24 in question appeared for the first time. The position of the illuminated dots 24 supplies two items of information in the reference framework 22. For one thing, the position of the respective luminous dot in the image field 15 is obtained irrespective of its shift. For another, an item of information about the time at which the dot lit up is obtained, even though this information is not necessary for some variants of PAL microscopy.

Figure 9:
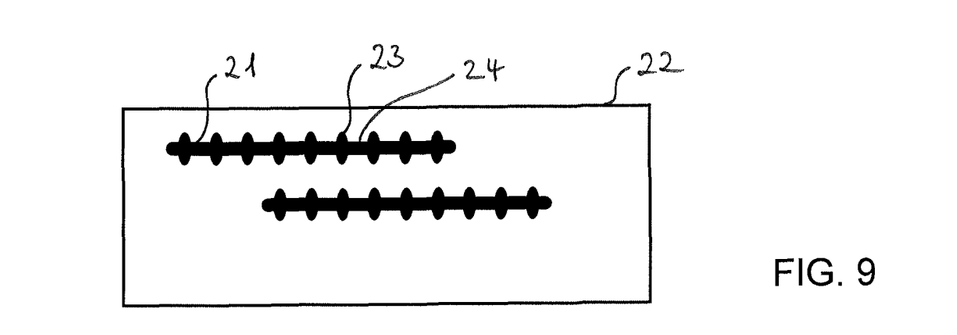
FIG. 9 depicts a representation similar to FIG. 7 for a particular type of operation of the variant according to FIGS. 6 to 8.

Knowledge about the shift of the image field 15 is important for the time scaling of the reference framework 22. If, for example, non-linearities of the scanning movement or a lack of resolution of a measurement of the scanning movement are problematic here, a periodic modulation of a focus parameter of the imaging of the sample field onto the image field will additionally be carried out. Thus, as a result, the detection point-spread distribution is modulated, with the result that a luminous dot has a diameter of a different size. The light trail 21 thus has widened areas 23 and non-widened areas 24 which match the modulation of the focus parameter. In known modulation, the scaling in the horizontal axis can thus be obtained particularly easily from the reference framework 22. The modulation of the focus parameter, for example, the detection point-spread function, may be carried out such that it is only just detectable in the light trail 21. A widening that is too great and ultimately a loss of resolution is thereby avoided as far as possible.

The invention claimed is:

1. A method of PAL microscopy, wherein
   placing a sample comprising fluorescence emitters into a wide-field microscope which has an optical resolution and comprises a spatially resolving detector having a radiation-sensitive detector surface,
   repeating several times a sequence of an isolation step and an imaging step, wherein each isolation step prepares a set of fluorescing emitters in which each fluorescing emitter is spaced apart from all neighboring fluorescing emitters by a minimum distance which is resolvable by the optical resolution of the wide-field microscope, and each imaging step images the fluorescing emitters by the wide-field microscope and provides a single image which contains a radiation distribution of the emitters of the set prepared in the immediate previous isolation step, wherein a sample area is imaged into an image area on the radiation-sensitive detector surface of the spatially-resolving detector,
   wherein the image area is smaller than the radiation-sensitive detector surface to obtain a single image, and the image area is shifted across the detector surface between successive imaging steps, with the result that in different imaging steps, the same sample area is imaged onto different, adjacent positions of the radiation-sensitive detector surface in order to determine information about changes in the sample area between different single images, and
   in each single image a position of a center of the radiation distribution is determined for each prepared emitter with a precision higher than the optical resolution of the wide-field microscope, and
   the positions of the centers of the prepared emitters in the single images are combined to a total image representing the sample with a resolution higher than the optical resolution of the wide-field microscope.

2. The method according to claim 1, wherein the same sample area is imaged onto the different, adjacent positions sequentially in time.

3. The method according to claim 1, wherein the radiation-sensitive detector surface comprises several, adjacent radiation-sensitive detector surface parts, for each of which detection data can be read out independently, wherein the image area is placed intermittently on alternating ones of the several radiation-sensitive detector surface parts and the detection data are read out for each radiation-sensitive detector surface part, while the image area is placed on another one of the several radiation-sensitive detector surface parts.

4. The method according to claim 1, wherein a shift of the image area is matched to a read-out of the detector and wherein detection data associated to several different shift positions of the image area are read out in one read-out process.

5. The method according to claim 4, wherein a position of the image area is shifted in steps across the radiation-sensitive detector surface, and the detection data is read out only after a plurality of steps, and wherein the detection data read out each position of the area forms one of the single images.

6. The method according to claim 4, wherein the detector comprises a 2D CCD detector which comprises on a read-out edge and a horizontal shift register located at the read-out edge, a detector area which is shaded from radiation and which lies between the read-out edge and the radiation-sensitive detector surface, and wherein the single images are recorded by shifting the image area in steps across the radiation-sensitive detector surface and by controlling the detector such that charges of one single image produced are transferred firstly into the detector area shaded from radiation and then from there into the horizontal shift register while charges of a next single image are already recorded at the radiation-sensitive surface.

7. The method according to claim 1, wherein during shifting of the image area between the successive image steps at least one of the following is effected: an illumination of the sample is deactivated, transmission of the imaging is deactivated and radiation sensitivity of the detector is deactivated.

8. The method according to claim 1, wherein the sample is excited, synchronized with shifting of the image area.

9. The method according to claim 1, wherein the emitters are activated by means of optical radiation to an activated state and can be excited to emit particular fluorescence radiation only in the activated state and wherein the isolation step comprises to illuminate the sample by the optical radiation such that the certain proportion of the activated emitters are spaced apart from neighboring activated emitters by the minimum distance.

10. The method according to claim 9, wherein the optical radiation is of a same wavelength as radiation used for fluorescence excitation of the emitters.

11. The method according to claim 9, wherein the optical radiation is of a wavelength other than the wavelength of radiation used for fluorescence excitation of the emitters.

12. A wide-field microscope for high-resolution PAL microscopy, comprising:
a spatially-resolving detector which includes a radiation-sensitive detector surface,
an imaging lens system which images a sample area of a sample comprising emitters onto the radiation-sensitive detector surface of the detector at an optical resolution, wherein the imaging lens system images the sample area onto an image area which is smaller than the radiation-sensitive detector surface, and comprises a controllable scanning device to shift the image area across the radiation-sensitive detector surface, and
a control device which
controls operation of the microscope to perform an isolation step at the sample preparing the labels such that at least a certain proportion of the emitters are fluorescing and isolated and spaced apart from neighboring activated emitters by a minimum distance which is resolvable by the optical resolution, and
controls operation of the microscope to perform an imaging step of the fluorescing emitters to obtain an image which contains a radiation distribution for each prepared emitter, wherein the control device reads out detection data of the detector, and controls the scanning device such that the same sample area is imaged onto different, adjacent positions of the image area, and information about changes in the sample area between different imaging steps is determined on the basis of the detection data read out providing a single image which contains a radiation distribution for each prepared emitter, and
wherein the control device determines from the single image a position of a center of the radiation distribution for each prepared emitter with precision higher than the optical resolution, and
wherein the control device repeats the isolation step and the imaging step and collects the determined positions to a total image having a resolution higher than the optical resolution.

13. The wide-field microscope according to claim 12, wherein the control device controls the scanning device such that the same sample area is imaged to the different, adjacent positions of the image area sequentially in time.

14. The wide-field microscope according to claim 12, wherein the detector comprises several, adjacent detector surface parts, for each of which detection data can be read out independently, and wherein the control device controls the scanning device such that it places the image area intermittently on alternating ones of the several detector surface parts and the control device reads out the detection data for each detector surface part, while the image field is placed on another one of the several detector surface parts.

15. The wide-field microscope according to claim 12, wherein the control device controls the scanning device and reads the detector such that detection data read out in one read-out process are associated to several different positions of the image area.

16. The wide-field microscope according to claim 15, wherein the control device controls the scanning device such that it shifts a position of the image area in steps across the radiation-sensitive detector surface, and the control device reads out the detection data only after several shifts, and wherein the control device allocates in the detection data read out, each position of the image area to one of the single images.

17. The wide field microscope according to claim 13, wherein the detector comprises a 2D CCD detector which comprises a horizontal shift register located at a read-out edge and a detector area which is shaded from radiation and which lies between the read-out edge and the radiation-sensitive detector surface, and wherein the control device controls the scanning device such that to record the single images by shifting the image area in steps across the radiation-sensitive detector surface and controls the detector such that charges of one single images produced are transferred firstly into the detector area shaded from of radiation and then from there into the horizontal shift register while charges of a next single image are already recorded at the radiation-sensitive surface.

18. The wide-field microscope according to claim 12, further comprising at least one of the following: a deactivation device for deactivating a sample illumination, a deactivation device for deactivating a transmission of an imaging beam path, and a deactivating device for deactivating the detector, wherein the scanning device switches on the deactivating device while the position of the image field is shifted.

19. The wide-field microscope according to claim 12, further comprising a sample excitation source for high-resolution PAL microscopy and wherein the control device controls the sample excitation source and the scanning device in an operation synchronous with each other.

20. The wide-field microscope according to claim 12, further comprising a switching radiation source emitting switching radiation activating the emitters to an activated state only in which they are excitable to emit particular fluorescence radiation and wherein the control device illuminates the sample by the optical radiation in the isolation step such that the certain proportion of the activated labels are spaced apart from neighboring activated emitters by the minimum distance.

21. The wide-field microscope according to claim 20, further comprising a excitation radiation source for fluorescence excitation of the emitters wherein the excitation radiation source emits excitation radiation at a different wavelength than the switching radiation source.

22. The wide-field microscope according to claim 12, further comprising a radiation source emitting radiation activating the emitters to an activated state only in which they are excitable to emit particular fluorescence radiation and emitting excitation radiation source for fluorescence excitation of the labels wherein the control device illuminates the sample by the radiation in the isolation step such that the certain proportion of the activated emitters are spaced apart from neighbouring activated emitters by the minimum distance.

* * * * *